United States Patent
Lv et al.

(10) Patent No.: US 10,414,767 B2
(45) Date of Patent: Sep. 17, 2019

(54) DEUTERATED QUINAZOLINONE COMPOUND AND PHARMACEUTICAL COMPOSITION COMPRISING SAME

(71) Applicant: Suzhou Zelgen Biopharmaceuticals Co., Ltd., Jiangsu (CN)

(72) Inventors: Binhua Lv, Jiangsu (CN); Chengwei Li, Jiangsu (CN)

(73) Assignee: Suzhou Zelgen Biopharmaceuticals Co., Ltd., Kunshan, Jiangsu (CN)

(*) Notice: Subject to any disclaimer, the term of this patent is extended or adjusted under 35 U.S.C. 154(b) by 0 days.

(21) Appl. No.: 15/115,316

(22) PCT Filed: Jan. 30, 2015

(86) PCT No.: PCT/CN2015/071996
§ 371 (c)(1),
(2) Date: Jun. 19, 2017

(87) PCT Pub. No.: WO2015/113521
PCT Pub. Date: Aug. 6, 2015

(65) Prior Publication Data
US 2017/0305911 A1    Oct. 26, 2017

(30) Foreign Application Priority Data

Jan. 30, 2014 (CN) .................. 2014 1 0044620
Feb. 20, 2014 (CN) .................. 2014 1 0058184

(51) Int. Cl.
*A61K 31/52* (2006.01)
*C07D 473/34* (2006.01)
*C07D 487/04* (2006.01)
*A61K 9/48* (2006.01)

(52) U.S. Cl.
CPC .......... *C07D 487/04* (2013.01); *A61K 9/4866* (2013.01); *A61K 31/52* (2013.01); *C07D 473/34* (2013.01); *C07B 2200/05* (2013.01)

(58) Field of Classification Search
None
See application file for complete search history.

(56) References Cited

U.S. PATENT DOCUMENTS 6,603,008 B1 * 8/2003 Ando ................... C07D 405/14
546/269.7
2012/0178767 A1    7/2012 Ulrich

FOREIGN PATENT DOCUMENTS

| CA | 2759724 A1 | 10/2010 |
|---|---|---|
| CN | 16064-44 A | 4/2005 |
| CN | 101031569 A | 9/2007 |
| CN | 102458410 A | 5/2012 |
| EA | 201101507 A1 | 5/2012 |
| EA | 201270184 A1 | 8/2012 |
| WO | 03035075 A1 | 5/2003 |
| WO | 2005113556 A1 | 12/2005 |
| WO | 2010123931 A1 | 10/2010 |
| WO | 2011008302 A1 | 1/2011 |
| WO | 2011011550 A1 | 1/2011 |
| WO | 2012097000 A1 | 7/2012 |
| WO | 102647987 A | 8/2012 |
| WO | 2015179772 A1 | 11/2015 |
| WO | WO-2015179772 A1 * | 11/2015 ............. A61K 31/52 |

OTHER PUBLICATIONS

Byrn, Stephen. Solid-State Chemistry of Drugs, 2nd Ed. (1999), Ch. 11 Hydrates and Solvates, 233-247.*
Rouhi, A.M. Chem. & Eng. News, (2003), 81(8), 32-35.*
Morissette, Sherry. Adv. Drug Delivery Rev. 2004, 56, 275-300.*
Auto-immune Diseases: MedlinePlus. (2014). Web: <https://www.nlm.nih.gov/medlineplus/autoimmunediseases.html>.*
WebMD: Inherited Metabolic Disorders.: Types, Causes, Symptoms and Treatments. (2014). Web: <http://www.webmd.com/a-to-z-guides/inherited-metabolic-disorder-types-and-treatments?page=2>.*
Infections: MedlinePlus. (2016) Web: < https://www.nlm.nih.gov/medlineplus/infections.html>.*

(Continued)

*Primary Examiner* — Emily A Bernhardt
*Assistant Examiner* — Laura M Daniel
(74) *Attorney, Agent, or Firm* — Panitch Schwarze Belisario & Nadel LLP

(57) ABSTRACT

Deuterated quinazolinone compounds and pharmaceutical compositions containing such compounds are provided. In particular, deuterated quinazolinone compounds of formula (I) are provided, as well as pharmaceutical compositions containing such compounds or crystal form, pharmaceutically acceptable salts, hydrates or solvates thereof. The deuterated quinazolinone compounds of formula (I) can be used for treating and/or preventing PI3K kinase-associated diseases, such as cancer, cell proliferative diseases and the like.

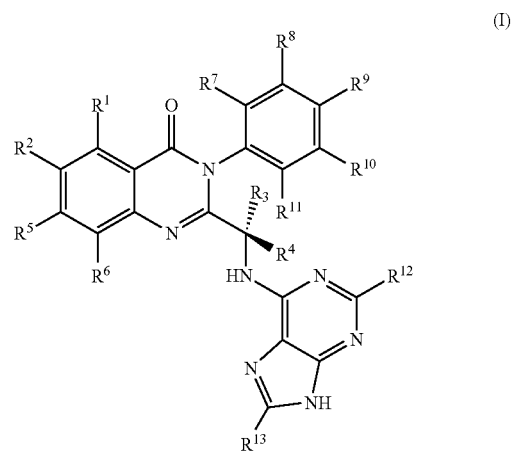

20 Claims, No Drawings

(56) References Cited

OTHER PUBLICATIONS

Myeloproliferative disorders: University of Maryland Medical Center. (2016).Web: <http://umm.edu/health/medical/altmed/condition/myeloproliferative-disorders>.*
Engleman, Jeffrey. Nature Reviews. vol. 9. 550-562 (2009).*
MedicineNet.com (2004) Web<http://www.medterms.com>.*
Tonn, G.R. Biological Mass Spectrometry vol. 22 Issue 11, pp. 633-642 (1993).*
WebMD. What is Leukemia. (2017). Web: <https://www.webmd.com/cancer/lymphoma/understanding-leukemia-basics#2>.*
The American Cancer Society. Can Non-Hodgkin Lymphoma be prevented? (2018). Web: <https://www.cancer.org/cancer/non-hodgkin-lymphoma/causes-risks-prevention/prevention.html>.*
Daniel C. Brookings, Ch. 8.15, "The Discovery and Development of Seletalisib: A Potent and Selective Pl3Kd Inhibitor or Inflammatory Diseases," Comprehensive Medicinal Chemistry III, Jun. 15, 2017, p. 402, (better copy than provided by Applicants).*
Int'l Search Report dated May 11, 2015 in Int'l Application No. PCT/CN2015/071996.
Extended European Search Report dated May 17, 2017 in EP Application No. 15743414.3.
Foster, "Deuterium Isotope Effects in the Metabolism of Drugs and Xenobiotics: Implications for Drug Design", Advances in Drug Research, vol. 14, pp. 1-40 (Jan. 1, 1985).
Winkler et al., "Pl3K-d and Pl3K-g Inhibition by IPI-145 Abrogates Immune Responses and Suppresses Activity in Autoimmune and Inflammatory Disease Models" Chemistry and Biology, vol. 20, No. 11, pp. 1364-1374 (Nov. 1, 2013).
Search Report dated Dec. 18, 2017 in RU Application No. 2016135192/04.
Office Action dated Jun. 16, 2017 in CA Applicatinon No. 2,956,773.
Chung et al., "Ibrutinib, Obinutuzumab, Idelalisib, and Beyond: Review of Novel and Evolving Therapies for Chronic Lymphocytic Leukemia", Pharmacotherapy, 2014, 1298-1316.
Daniel C. Brookings, Ch. 8.15, "The Discovery and Development of Seletalisib: A Potent and Selective Pl3Kd Inhibitor or Inflammatory Diseases," Comprehensive Medicinal Chemistry III, Jun. 15, 2017, p. 402.
CHMP Assessment Report, European Medicines Agency Science Medicines Health, 132 Pages, Jul. 2014.

* cited by examiner

DEUTERATED QUINAZOLINONE COMPOUND AND PHARMACEUTICAL COMPOSITION COMPRISING SAME

CROSS-REFERENCE TO RELATED APPLICATION

This application is a Section 371 of International Application No. PCT/CN2015/071996, filed Jan. 30, 2015, which was published in the Chinese language on Aug. 6, 2015, under International Publication No. WO 2015/113521 A1, and the disclosure of which is incorporated herein by reference.

FIELD OF THE INVENTION

The present invention relates to the field of pharmaceutics. Specifically, the present invention relates to a new deuterated quinazolinone compound, and pharmaceutical compositions comprising same.

BACKGROUND OF THE INVENTION

Phosphoinositide 3-kinases (PI3Ks) is a enzyme which specifically catalyze the phosphorylation of 3rd position hydroxyl in phosphatidylinositol (PI) and its derivatives, and produce the phosphatidylinositol-3,4,5-triphosphate (PI3P) which serve as the second messenger. Signal transduction mediated by PI3Ks involves in regulations of several cell functions such as cell division, differentiation, apoptosis, metabolism, angiogenesis, and plays an important role in the activation of a variety of cell biological functions. Studies in recent years have shown that signaling pathways consisted of PI3Ks and the downstream molecular protein kinase B (PKB or Akt) are closely associated with the genesis and development of cancer, regulating tumor cell proliferation, apoptosis and promoting tumor angiogenesis, etc.

Quinazolinone compounds and derivatives thereof are a class of inhibitors for Phosphoinositide 3-kinase. A series of quinazoline derivatives has been disclosed in WO03035075 and WO2005113556. Among them the compound GS-1101, of which the chemical name is (S)-2-(1-(9H-purin-6-yl-amino)propyl)-5-fluoro-3-phenyl quinazoline-4(3H)-ketone, is a selective PI3K kinase inhibitor, and it can be used in the treatment of cancer and cell proliferative diseases, and other related diseases. At present, the compound is in the Phase III clinical trials of treating chronic lymphocytic leukemia and non-Hodgkin lymphomas.

Phosphoinositide 3-kinase (PI3K) is one of the important targets for the development of new anti-tumor drugs. However, except for rapamycin and homologs, the research progress of inhibition of PI3K signal transduction pathway is relatively slow, especially the development of specific inhibitors for PI3K subtypes (such as type I PI3K including p110α, p110β, p110δ, etc.) is still very challenging.

Therefore, there is still a need in the art to develop compounds having PI3K kinase inhibitory activity or better pharmacodynamic/pharmacokinetics properties.

SUMMARY OF THE INVENTION

The object of the present invention is to provide a type of novel compounds having PI3K kinases inhibitory activity and/or better pharmacodynamic/pharmacokinetics properties, and uses thereof.

In the first aspect of the present invention, it provided a deuterated quinazolinone compound of formula (I), or a crystal form, pharmaceutically acceptable salt, hydrate or solvate thereof:

(I)

Wherein $R^1$ and $R^2$ are independently hydrogen, deuterium or halogen;

$R^3$ is selected from: hydrogen, deuterium, $CH_3$, $CH_2D$, $CHD_2$, $CD_3$, $CH_2CH_3$, $CD_2CH_3$, $CH_2CD_3$ and $CD_2CD_3$;

$R^4$, $R^5$, $R^6$, $R^7$, $R^8$, $R^9$, $R^{10}$, $R^1$, $R^{12}$ and $R^{13}$ are each independently hydrogen or deuterium;

with the proviso that at least one of $R^1$, $R^2$, $R^3$, $R^4$, $R^5$, $R^6$, $R^7$, $R^8$, $R^9$, $R^{10}$, $R^{11}$, $R^{12}$ or $R^{13}$ is deuterated or deuterium.

In another preferred embodiment, the deuterium isotope content at the deuterium-substituted position is at least greater than natural isotopic deuterium content (about 0.015%), preferably greater than 30%, more preferably greater than 50%, more preferably greater than 75%, more preferably greater than 95%, more preferably greater than 99%.

In another preferred embodiment, the compound of formula (I) contains at least one deuterium atom, more preferably three deuterium atoms, more preferably four deuterium atoms, more preferably 6 deuterium atoms.

In another preferred embodiment, enantiomeric excess of the compound of formula (I) is greater than 95%, more preferably greater than 98%, more preferably greater than 99%.

In another preferred embodiment, $R^1$ is fluorine and/or $R^2$ is hydrogen.

In another preferred embodiment, $R^4$ is hydrogen or deuterium.

In another preferred embodiment, $R^5$, $R^6$, $R^7$, $R^8$, $R^9$, $R^{10}$, $R^{11}$, $R^{12}$ and $R^{13}$ are independently hydrogen or deuterium.

In another preferred embodiment, $R^1$ is halogen, such as fluorine, chlorine, bromine, iodine.

In another preferred embodiment, $R^1$ is fluorine.

In another preferred embodiment, $R^3$ is $CH_3$, $CH_2D$, $CHD_2$, $CD_3$, $CH_2CH_3$, $CD_2CH_3$, $CH_2CD_3$ or $CD_2CD_3$.

In another preferred embodiment, $R^4$ is deuterium.

In another preferred embodiment, $R^{12}$ is deuterium and/or $R^{13}$ is deuterium.

In another preferred embodiment, $R^{12}$ is deuterium.

In another preferred embodiment, $R^{13}$ is deuterium

In another preferred embodiment, the compound is one of the following compounds, or a pharmaceutical acceptable salt thereof:

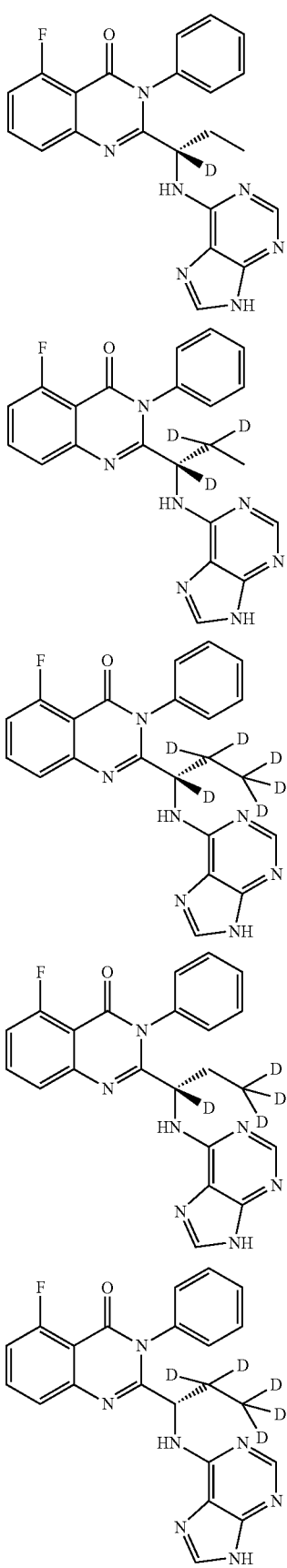
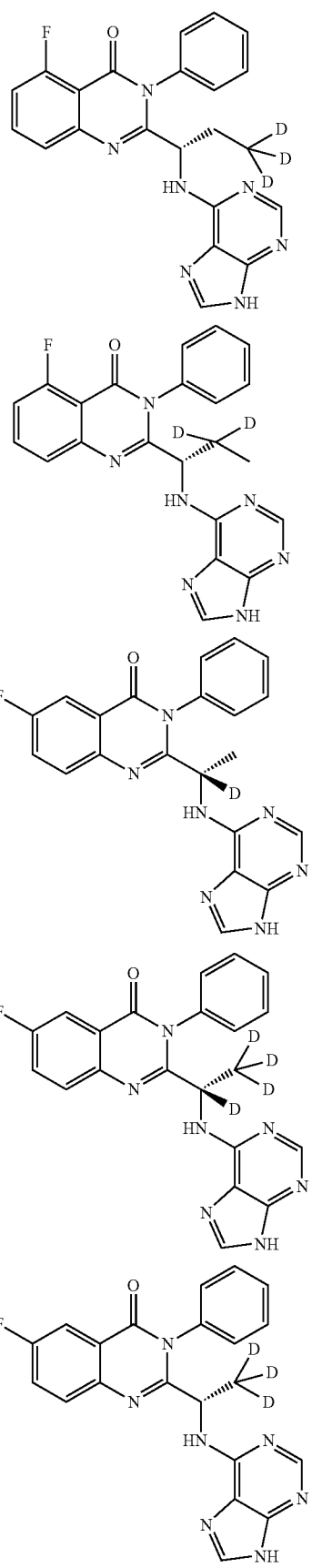

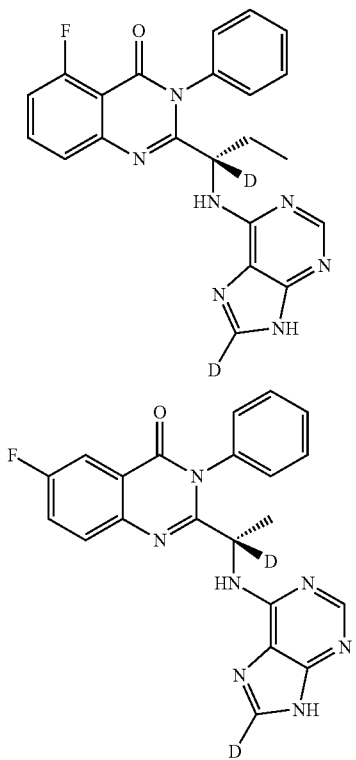
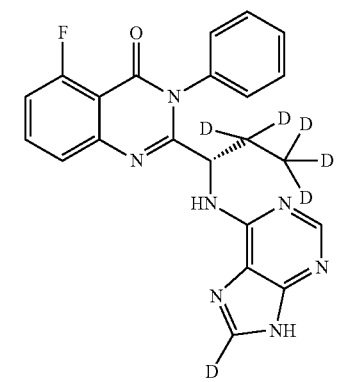
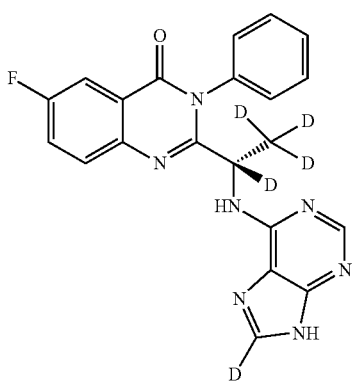
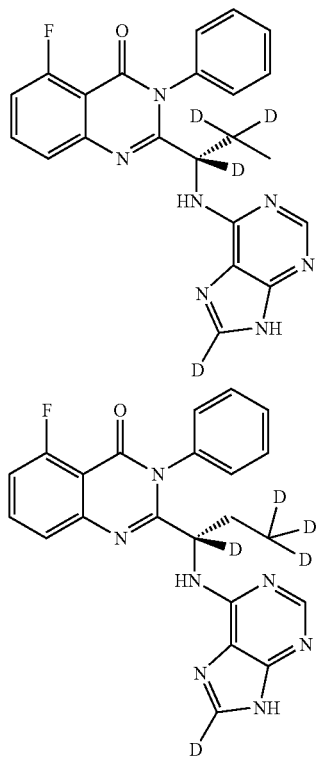
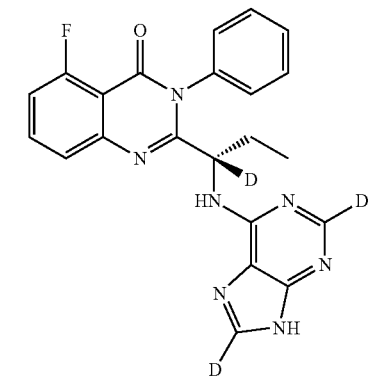

-continued
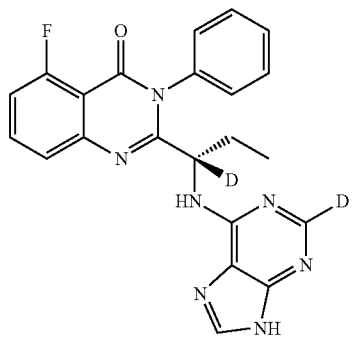
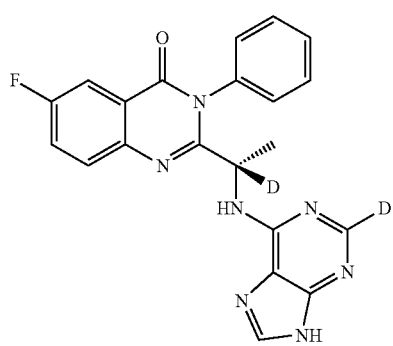
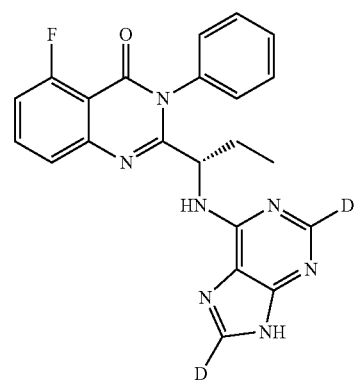
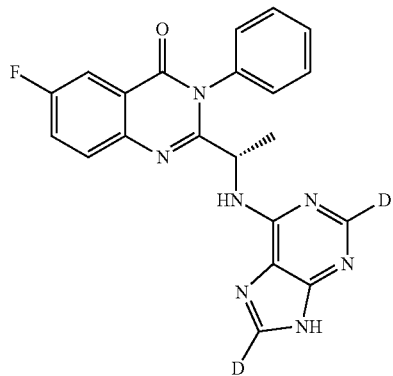
-continued
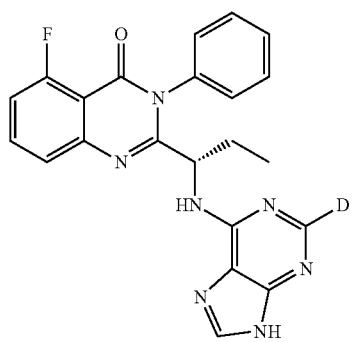
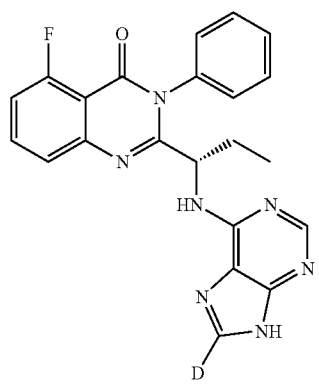
In another preferred embodiment, the compound is one of the following compounds, or a pharmaceutical acceptable salt thereof:
(S)-2-(1-(9H-purin-6-yl-amino)-(1-d-propyl))-5-fluoro-3-phenyl quinazoline-4(3H)-ketone
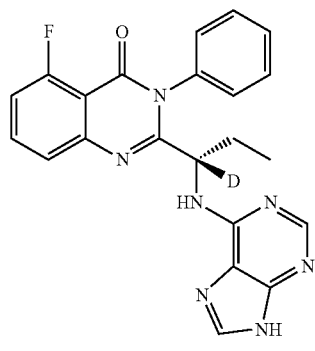 [SMILES: [2H][C@@](CC)(Nc1ncnc2[nH]cnc12)c1nc2cccc(F)c2c(=O)n1-c1ccccc1]

9

(S)-2-(1-(9H-purin-6-yl-amino)-(1,2,2-d₃-propyl))-5-fluoro-3-phenyl quinazoline-4(3H)-ketone

10

(S)-2-(1-(9H-purin-6-yl-amino)-(2,2,3,3,3-d₅-propyl))-5-fluoro-3-phenyl quinazoline-4(3H)-ketone

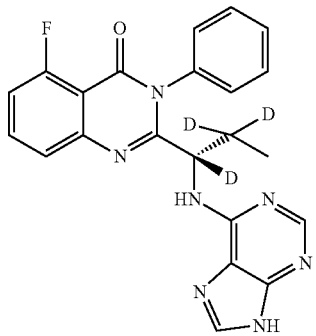 [SMILES: [2H]C([2H])(C)[C@]([2H])(Nc1ncnc2[nH]cnc12)c1nc2cccc(F)c2c(=O)n1-c1ccccc1]

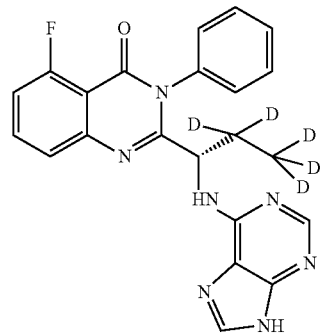

(S)-2-(1-(9H-purin-6-yl-amino)-(1,2,2,3,3,3-d₆-propyl))-5-fluoro-3-phenyl quinazoline-4(3H)-ketone (S)-2-(1-(9H-purin-6-yl-amino)-(3,3,3-d₃-propyl))-5-fluoro-3-phenyl quinazoline-4(3H)-ketone

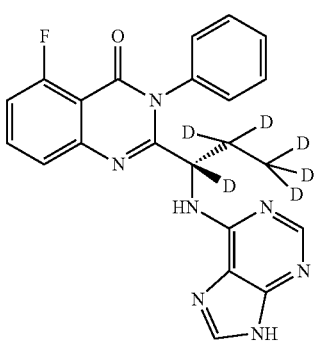 [SMILES: [2H]C([2H])([2H])C([2H])([2H])[C@]([2H])(Nc1ncnc2[nH]cnc12)c1nc2cccc(F)c2c(=O)n1-c1ccccc1]

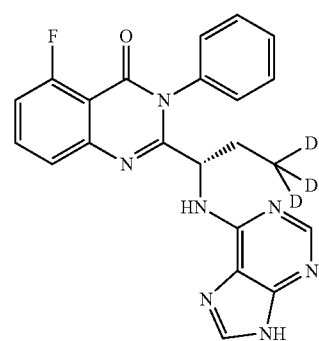

(S)-2-(1-(9H-purin-6-yl-amino)-(1,3,3,3-d₄-propyl))-5-fluoro-3-phenyl quinazoline-4(3H)-ketone (S)-2-(1-9H-purin-6-yl-amino)-2,2-d₂-propyl))-5-fluoro-3-phenyl quinazoline-4(3H)-ketone

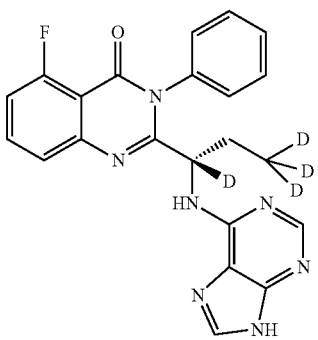 [SMILES: [2H]C([2H])([2H])C[C@]([2H])(Nc1ncnc2[nH]cnc12)c1nc2cccc(F)c2c(=O)n1-c1ccccc1]

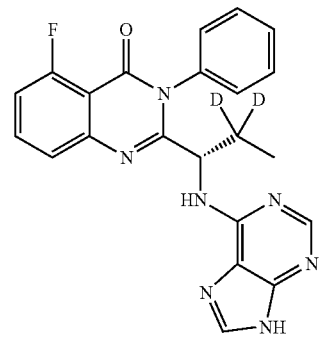 [SMILES: [2H]C([2H])(C)[C@H](Nc1ncnc2[nH]cnc12)c1nc2cccc(F)c2c(=O)n1-c1ccccc1]

11

(S)-2-(1-(9H-purin-6-yl-amino)-(1-d-ethyl))-6-fluoro-3-phenyl quinazoline-4(3H)-ketone

12

(S)-2-(1-(9H-purin-2,8-d$_2$-6-yl-amino)-(1-d-propyl))-5-fluoro-3-phenyl quinazoline-4(3H)-ketone

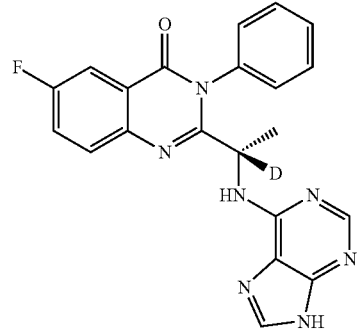 [SMILES: [2H][C@@](C)(Nc1ncnc2[nH]cnc12)c1nc2ccc(F)cc2c(=O)n1-c1ccccc1]
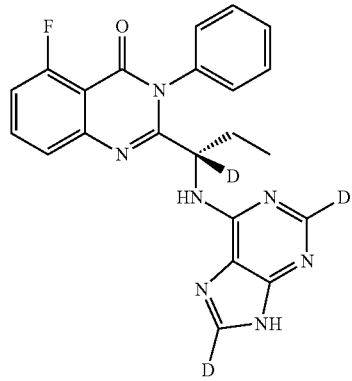

(S)-2-(1-(9H-purin-6-yl-amino)-(2,2,2-d$_3$-ethyl))-6-fluoro-3-phenyl quinazoline-4(3H)-ketone (S)-2-(1-(9H-purin-2,8-d$_2$-6-yl-amino)-propyl)-5-fluoro-3-phenyl quinazoline-4(3H)-ketone

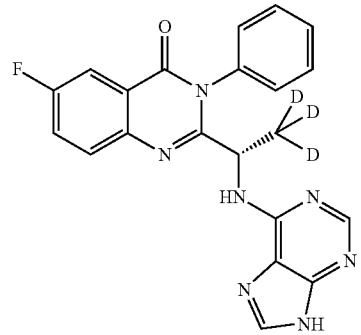 [SMILES: [2H]C([2H])([2H])[C@H](Nc1ncnc2[nH]cnc12)c1nc2ccc(F)cc2c(=O)n1-c1ccccc1]
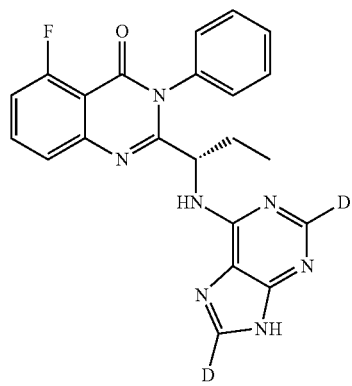

(S)-2-(1-(9H-purin-8-d-6-yl-amino)-(1-d-propyl))-5-fluoro-3-phenyl quinazoline-4(3H)-ketone (S)-2-(1-(9H-purin-8-d-6-yl-amino)-propyl)-5-fluoro-3-phenyl quinazoline-4(3H)-ketone

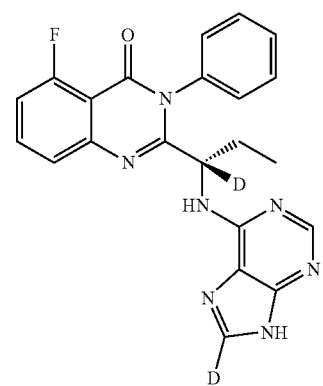 [SMILES: [2H]c1nc2c(N[C@@]([2H])(CC)c3nc4cccc(F)c4c(=O)n3-c3ccccc3)ncnc2[nH]1]
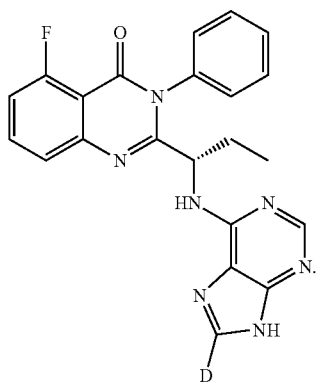 [SMILES: [2H]c1nc2c(N[C@@H](CC)c3nc4cccc(F)c4c(=O)n3-c3ccccc3)ncnc2[nH]1]

In another preferred embodiment, the compound is

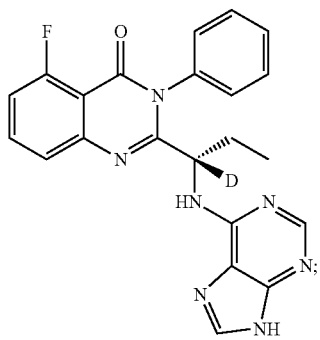 [SMILES: [2H][C@@](CC)(Nc1ncnc2[nH]cnc12)c1nc2cccc(F)c2c(=O)n1-c1ccccc1]

which possesses the following characteristics: MS calculated: 416; MS found: 417 (M+H)⁺, 439 (M+Na)⁺.

In another preferred embodiment, the compound is

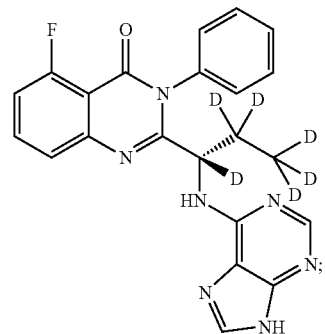 [SMILES: [2H]C([2H])([2H])C([2H])([2H])[C@]([2H])(Nc1ncnc2[nH]cnc12)c1nc2cccc(F)c2c(=O)n1-c1ccccc1]

which possesses the following characteristics: MS calculated: 421; MS found: 422 (M+H)⁺, 444 (M+Na)⁺.

In another preferred embodiment, the compound is

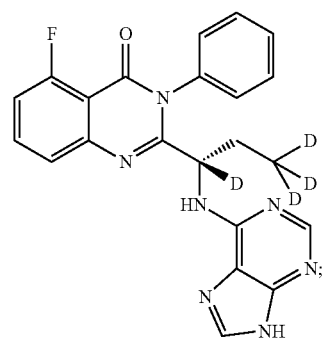 [SMILES: [2H]C([2H])([2H])C[C@]([2H])(Nc1ncnc2[nH]cnc12)c1nc2cccc(F)c2c(=O)n1-c1ccccc1]

which possesses the following characteristics: MS calculated: 419; MS found: 420 (M+H)⁺, 442 (M+Na)⁺.

In another preferred embodiment, the compound is

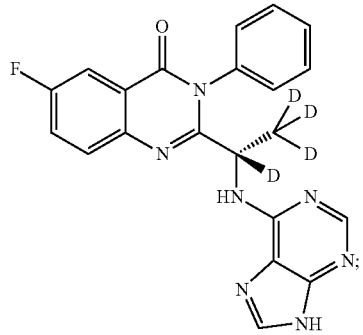 [SMILES: [2H]C([2H])([2H])[C@]([2H])(Nc1ncnc2[nH]cnc12)c1nc2ccc(F)cc2c(=O)n1-c1ccccc1]

which possesses the following characteristics: MS calculated: 405; MS found: 406 (M+H)⁺, 428 (M+Na)⁺.

In another preferred embodiment, the compound is

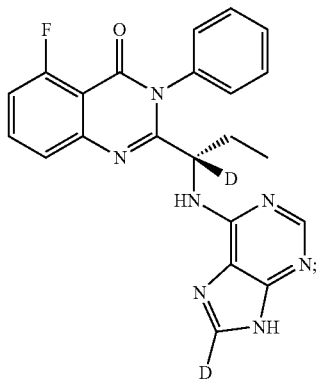 [SMILES: [2H]c1nc2c(N[C@@]([2H])(CC)c3nc4cccc(F)c4c(=O)n3-c3ccccc3)ncnc2[nH]1]

which possesses the following characteristics: MS calculated: 417; MS found: 418 (M+H)⁺, 440 (M+Na)⁺.

In another preferred embodiment, the compound is

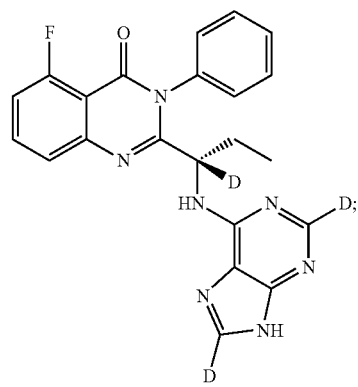

which possesses the following characteristics: MS calculated: 418; MS found: 419 (M+H)⁺, 441 (M+Na)⁺.

In another preferred embodiment, the compound is

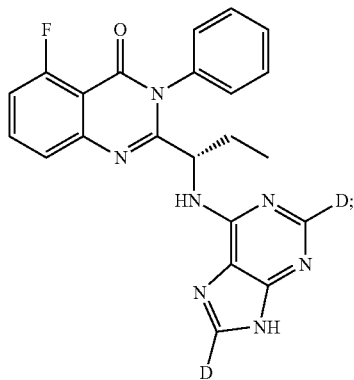

which possesses the following characteristics: MS calculated: 417; MS found: 418 (M+H)$^+$, 440 (M+Na)$^+$.

In another preferred embodiment, the compound is

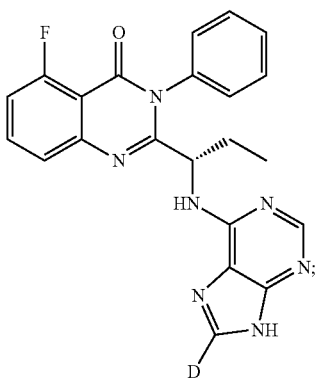 [SMILES: [2H]c1nc2c(N[C@@H](CC)c3nc4cccc(F)c4c(=O)n3-c3ccccc3)ncnc2[nH]1]

which possesses the following characteristics: MS calculated: 416; MS found: 417 (M+H)$^+$, 439 (M+Na)$^+$.

In another preferred embodiment, undeuterinated compounds are not included in the compound.

In another preferred embodiment, the undeuterated compound is (S)-2-(1-(9H-purin-6-yl-amino) propyl)-5-fluoro-3-phenyl quinazoline-4(3H)-ketone.

In another preferred embodiment, the compound is prepared by the method described in examples 1-12.

In the second aspect of the present invention, it provided a method of preparing a pharmaceutical composition, which comprises the following step: mixing compounds of the first aspect of the present invention, or a crystal form, pharmaceutically acceptable salt, hydrate or solvate thereof with a pharmaceutically acceptable carrier to form a pharmaceutical composition.

In the third aspect of the present invention, it provided a pharmaceutical composition is provided, which comprises a pharmaceutically acceptable carrier and the compound of the first aspect of the present invention, or a crystal form, pharmaceutically acceptable salt, hydrate or solvate thereof.

In another preferred embodiment, the pharmaceutical composition is injection, capsule, tablet, pill, powder, or granule.

In another preferred embodiment, the pharmaceutical composition comprises other therapeutic medicines, and the other therapeutic medicines are medicines for treating cancers, cardiovascular diseases, inflammations, infections, autoimmune diseases, cell proliferative disorders, viral diseases, metabolic disorders, or medicine for organ transplant.

More preferably, the other therapeutic medicines comprise (but are not limited to): 5-fluorouracil, FOLFOX, Avastin™ (avastin, bevacizumab), bexarotene, bortezomib, calcitriol, canertinib, capecitabine, gemcitabine, carboplatin, celecoxib, cetuximab, cisplatin, dasatinib, digoxin, enzastaurin, erlotinib, etoposide, everolimus, fulvestrant, gefitinib, genistein, imatinib, irinotecan, lapatinib, lenalidomide, letrozole, leucovorin, matuzumab, oxaliplatin, Taxol (paclitaxel), docetaxel, panitumumab, PEGylated granulocyte colony stimulating factor (pegfilgrastin), peglated alfa-interferon, pemetrexed, Polyphenon® E, satraplatin, sirolimus, sunitinib (sutent), sulindac, taxotere, temozolomide (temodar), Torisel, temsirolimus, tipifarnib, trastuzumab, valproic acid, vinflunine, Volociximab, Vorinostat, sorafenib, Crizotinib, Lcotinib, lapatinib, Tofacitinib, PD-0332991 (Palbociclib), ambrisentan, doxorubicin, methotrexate, Prednisone, rituximab, CD40 and/or CD154-specific antibodies, fusion proteins, NF-kB inhibitors, non-steroidal anti-inflammatory drugs, clotting factor FXa inhibitors (such as rivaroxaban, etc.), anti-TNF antibodies, antibiotics such as calicheamicin, actinomycin, Adriamycin (doxorubicin), etc.

In the fourth aspect of the present invention, it provided a use of the compound of the first aspect of the present invention, or a crystal form, pharmaceutically acceptable salt, hydrate or solvate thereof in the preparation of pharmaceutical compositions that inhibit PI3K kinases.

In another preferred embodiment, the pharmaceutical composition of the invention can be used to treat the following diseases: cancers, cell proliferative disorders, inflammations, infections, or autoimmune diseases.

In another preferred embodiment, the cancers include (but are not limited to): lung cancer, breast cancer, prostate cancer, esophageal cancer, colorectal cancer, colon cancer, blood cancer (or malignant hematologic disease), osteosarcoma, kidney cancer, stomach cancer, liver cancer, or colorectal cancer.

In another preferred embodiment, the blood cancer (or malignant hematologic disease) is leukemia and lymphoma.

In another preferred embodiment, the lymphoma is chronic lymphocytic leukemia, acute lymphocytic leukemia, acute myeloid leukemia, multiple myeloma and chronic myeloid leukemia.

In the fifth aspect of the present invention, it provided a method of inhibiting PI3K kinases or a method of treating diseases (such as cancer, cell proliferative disorders, inflammation, infection, immune diseases) comprising the following steps: administering the compound of the first aspect of the present invention, or a crystal form, pharmaceutically acceptable salt, hydrate or solvate thereof, or administering the pharmaceutical composition of the third aspect of the present invention to a subject in need thereof.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Through research, the inventor has unexpectedly discovered that the deuterated quinazolinone compound or pharmaceutically acceptable salts thereof are obviously superior to the undeuterated compound in pharmacokinetic and/or pharmacodynamic properties, which, therefore, are more suitable to be used as PI3K kinases inhibitory compounds, and more suitable to be used in the preparation of medicines for treating cancers and diseases associated PI3K kinases. The present invention is completed on this basis.

Definitions

As used herein, "halogen" refers to F, Cl, Br, and I. More preferably, the halogen is selected from F, Cl and Br.

As used herein, "Superior pharmacokinetics and/or pharmacodynamic properties" refers to longer drug half-life ($t_{1/2}$), or higher drug exposure (AUC), or higher maximum drug concentration (Cmax), or lower drug clearance.

As used herein, "deuterated" means that one or more hydrogen in a compound or group is (are) replaced by deuterium. "Deuterated" may be mono-substituted, di-substituted, multiple-substituted or fully substituted. The term "one- or multiple-deuterated" and "deuterated for one or more times" can be used interchangeably.

As used herein, "undeuterated compound" refers to a compound, the ratio of deuterium atoms of which is not more than the natural isotopic deuterium content (about 0.015%).

In another preferred embodiment, deuterium isotope content at the deuterium substituted position is greater than the natural isotopic deuterium content (0.015%), more preferably greater than 50%, more preferably greater than 75%, more preferably greater than 95%, more preferably greater than 97%, more preferably greater than 99%, more preferably greater than 99.5%.

In another preferred embodiment, the compound of formula (I) contains at least one deuterium atoms, more preferably two deuterium atoms, more preferably three deuterium atoms, more preferably six deuterium atoms.

Preferably, in the compound of formula (I), N is $^{14}$N and/or O is $^{16}$O.

In another preferred embodiment, in the compound, $^{14}$N isotope content at the nitrogen atom position is ≥95%, preferably ≥99%.

In another preferred embodiment, in the compound, $^{16}$O isotope content at the oxygen atom position is ≥95%, preferably ≥99%.

Active Ingredients

As used herein, the term "the compound of the present invention" refers to the compound of formula (I). The term also comprises crystal forms, pharmaceutically acceptable salts, hydrates or solvates of the compound of formula (I).

Among which, the term "pharmaceutically acceptable salt" refers to a salt formed by the compound of the present invention and an acid or alkali which is suitable for a medicine. The pharmaceutically acceptable salts include inorganic and organic salts. A preferred type of salts are salts formed by the compounds of the present invention and an acid. Suitable salt-forming acids include, but are not limited to: inorganic acids such as hydrochloric acid, hydrobromic acid, hydrofluoric acid, sulfuric acid, nitric acid, phosphoric acid, and the like; organic acids such as formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, p-toluenesulfonic acid, benzenesulfonic acid, naphthalenesulfonic acid and the like; and amino acids such as proline, phenylalanine, aspartic acid, glutamic acid, and the like. Another preferred type of salts are salts formed by the compounds of the present invention and bases, e.g., alkali metal salts (e.g. sodium or potassium salts), alkaline earth metal salts (e.g. calcium or magnesium salts), ammonium salts (e.g., lower alkanol ammonium salts or other pharmaceutically acceptable amine salts), for example, methylamine salt, ethylamine salt, propylamine salt, dimethylamine salt, trimethylamine salts, diethylamine salts, triethylamine salts, tert-butyl amine salts, ethylenediamine salts, hydroxyethylamine salts, bi-hydroxyethylamine salts, tri-hydroxyethylamine salts, and amine salts formed by morpholine, piperazine, and lysine.

The term "solvate" refers to a complex of specific ratio formed by coordinating the compound of the present invention with solvent molecules. "Hydrate" refers to a complex formed by coordinating the compound of the present invention with water.

Moreover, the compounds of the present invention further comprise chiral enantiomers or despinners of quinazolinone compounds of formula (I).

Moreover, the compounds of the present invention further comprise prodrugs of quinazolinone compounds of formula (I). The term "prodrug" includes a type of compounds which have biological activity or non-activity, and would convert to the compound of formula (I) though metabolism or chemical reactions in the human body when administered by appropriate method, or the salt or solvate formed by a compound of formula (I). The prodrugs include (but are not limited to) the carboxylic acid ester, carbonic ester, phosphate, nitrate, sulfate, sulfone ester, sulfoxide esters, amino compounds, carbamates, azo compounds, phosphoramides, glucoside, ether, acetal of the compound, etc.

Preparation Method

Hereinafter the preparation of compounds of formula (I) will be described in detail, but such specific methods do not constitute any limitation to the present invention. The compounds of the invention may also be readily prepared by optionally combining various synthetic methods described in this specification or known in the art, such a combination can be readily performed by one of ordinary skill in the art to which the present invention belongs.

The methods used in the present invention for preparing the undeuterated quinazolinone compounds and physiologically compatible salts thereof are known. Preparation of corresponding deuterated quinazolinone compounds can be conducted by using the corresponding deuterated starting compound through the same synthesizing route. For example, a compound of formula (I) of the present invention can be prepared according to the method described in WO03035075, except that deuterated materials are used instead of non-deuterated materials.

Generally, in the preparation process, each reaction is generally conducted in an inert solvent, under room temperature to reflux temperature (such as 0° C.-200° C., preferably from 0° C.-100° C.). The reaction time is usually 0.1 hours-60 hours, preferably 0.5 to 48 hours.

The following general preparative route may be used in the synthesis of compounds of formula (I) of the present invention.

Synthetic route I

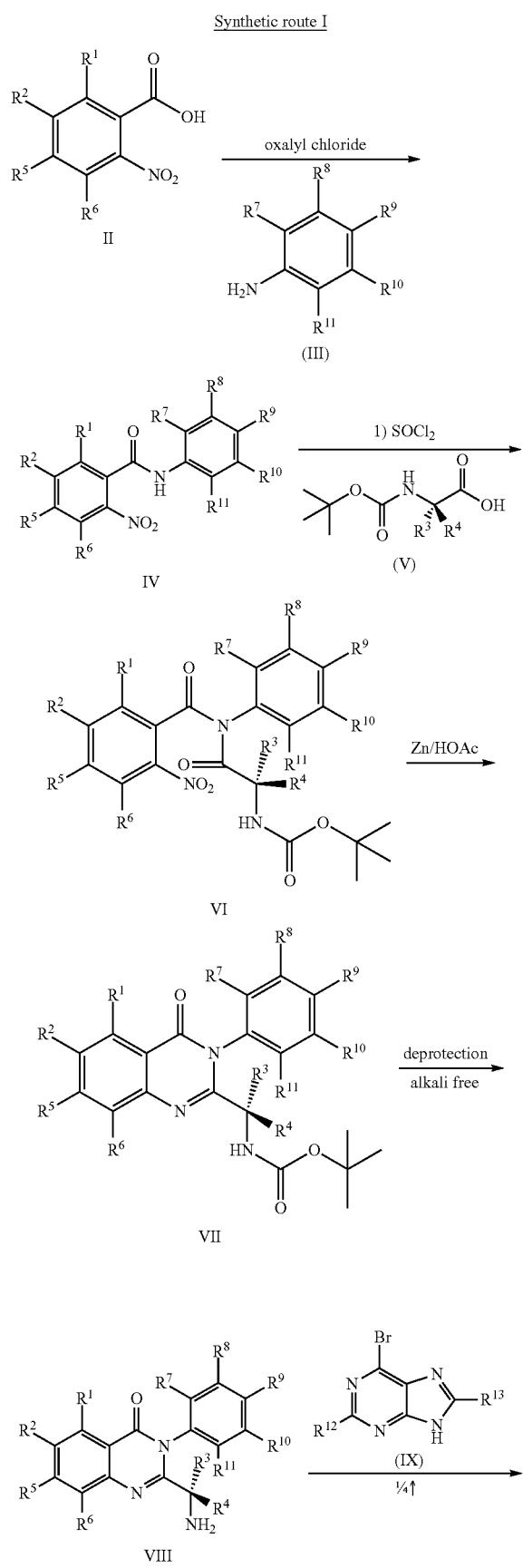

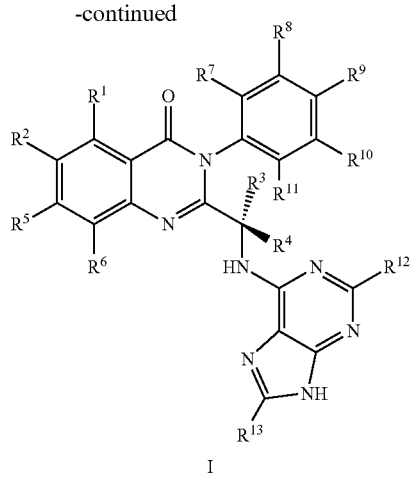

Wherein: $R^2$, $R^1$ are selected from H, D, F, Cl, Br, I; $R^3$, $R^4$, $R^5$, $R^6$, $R^7$, $R^8$, $R^9$, $R^{10}$, $R^{11}$, $R^{12}$ and $R^{13}$ are defined as above.

As shown in Synthetic route I, substituted m-nitrobenzoic acid compound II acylated with oxalyl chloride was used to react with substituted aniline III under alkaline condition to provide compound IV. The amidic hydrogen of compound IV is substituted by chlorine under the condition of sulfoxide chloride, and then compound IV reacts with Boc-protected deuterated amino acid V to obtain compound VI. Arylamine is obtained from the aryl nitro structure in compound VI under reduction condition such as zinc powder/acetic acid, stannous chloride, reduced iron powder or under catalytic hydrogenation conditions, such as palladium, platinum, Raney nickel and the like. Quinazoline ketone structure VII is obtained through ring closing reaction. Compound VII gets rid of Boc protection under the condition of trifluoroacetic acid/methylene chloride and hydrochloric acid/dioxane, and then it is alkali freed to get compound VIII. Finally, the compound I of the present invention is obtained from compound VIII boiling with 6-bromine purine or 6-bromine deuterated purine under alkaline condition in alcoholic solvent (such as ethanol, n-butanol and tertiary butyl alcohol) or tetrahydrofuran solvent. The above reactions are conducted in an inert solvent, such as dichloromethane, dichloroethane, acetonitrile, n-hexane, toluene, tetrahydrofuran, N,N-dimethylformamide, dimethylsulfoxide, acetic acid, butanol, propyl alcohol, etc., under a temperature of 0-200° C.

Deuterated compound V can be prepared by the following routes:

Synthetic route II

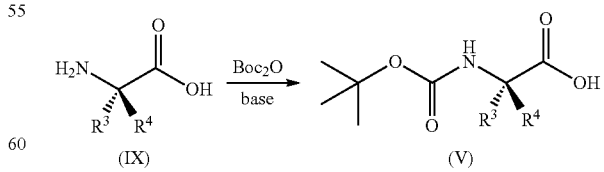

Wherein: $R^3$, $R^4$ are defined as above.

As shown in Synthetic route II, under alkaline conditions, deuterated amino acid IX reacts with di-tert-butyl dicarbonate to obtain N-Boc-protected amino acid V. Some deuterated amino acid IX is obtained through conventional deuterium method. Another deuterated amino acid IX can be purchased, such as (2S)-2-amino-4,4,4-d$_3$-butyric acid, (2S)-2-amino-3,3-d$_2$-butyric acid, (2S)-2-amino-2-d-butyric acid and (2S)-2-amino-2,3,3-d$_3$-butyric acid.

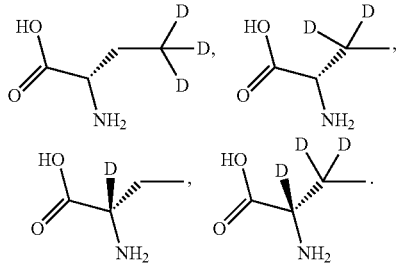

Pharmaceutical Composition and Administration Thereof

The compounds of the present invention possess outstanding activity of inhibiting PI3K kinases. Therefore, the compound of the present invention, and crystal forms, pharmaceutically acceptable inorganic or organic salts, hydrates or solvates thereof, and the pharmaceutical composition comprising the compound of the present invention as a main active ingredient can be used for treating, preventing and alleviating diseases mediated by PI3K kinases. Based on the prior art, the compounds of the invention can be used to treat the following diseases: cancers, cell proliferative disorders, inflammations, infections and autoimmune diseases.

The pharmaceutical composition of the invention comprises the compound of the present invention or pharmaceutically acceptable salts thereof in a safe and effective dosage range and pharmaceutically acceptable excipients or carriers. Wherein, the term "safe and effective dosage" refers to the amount of the compound which is enough to improve the patient's condition without any serious side effect. Generally, the pharmaceutical composition contains 1-2000 mg of the compounds of the invention per dose, preferably, 10-1000 mg of the compounds of the invention per dose. Preferably, "per dose" means one capsule or tablet.

"Pharmaceutically acceptable carrier" means one or more compatible solid or liquid fillers or gel materials, which are suitable for human, and must have sufficient purity and sufficiently low toxicity. "Compatibility" herein means that components of the composition can be blended with the compounds of the invention or with each other, and would not significantly reduce the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation on administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, active compounds are mixed with at least one conventional inert excipient (or carrier), such as sodium citrate or CaHPO$_4$, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in certain part of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agents, sweeteners, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

When the pharmaceutical compositions are used, a safe and effective amount of compound of the present invention is applied to a mammal (such as human) in need thereof, wherein the dose of administration is a pharmaceutically effective dose. For a person weighed 60 kg, the daily dose is usually 1-2000 mg, preferably 50-1000 mg. Of course, the particular dose should also depend on various factors, such as the route of administration, patient healthy status, which are well within the skills of an experienced physician.

Compared to non-deuterated compounds known in the prior art, the compounds of the present invention possess a number of advantages. The main advantages of the present invention are:

(1) The compounds of the present invention have a good inhibitory activity to protein kinase (such as PI3K kinase).

(2) The metabolism of the deuterated compounds in the organism is changed by deuterate technology, thus rendering the compound better pharmacokinetic parameters characteristic. In this case, the dose may be varied and a long-acting preparation can be formed to improve the applicability.

(3) The drug concentration of the compound in animals can be enhanced through substitution of deuterium for hydrogen in the compound due to the deuterium isotope effect, thus improving drug efficacy.

(4) The security compound may be improved through substitution of deuterium for hydrogen in the compound, since some metabolites is suppressed.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Example 1

Preparation of (S)-2-(1-(9H-purin-6-yl-amino)-(1-d-propyl))-5-fluoro-3-phenyl quinazoline-4(3H)-ketone (Compound 6)

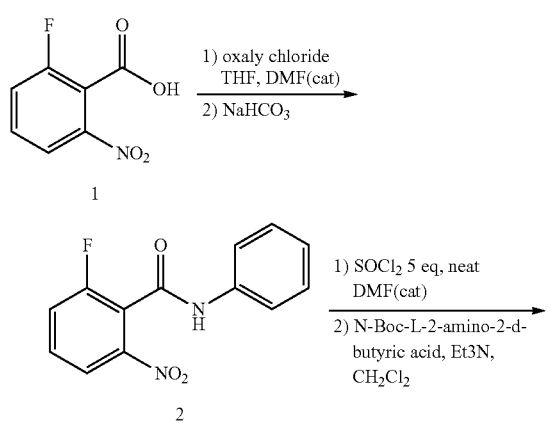

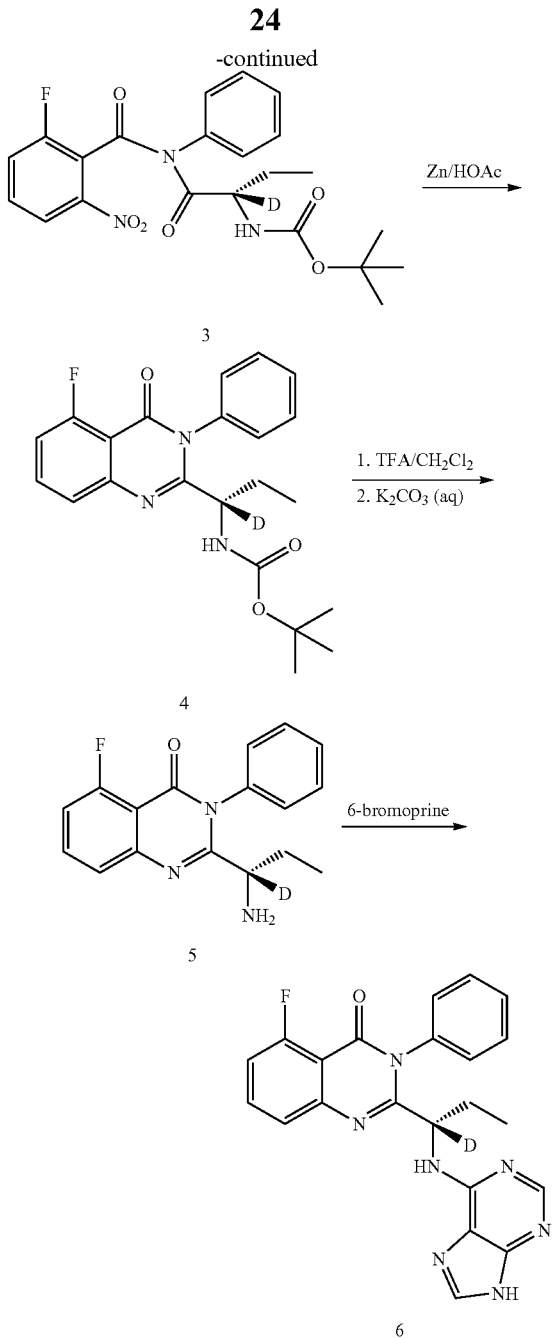

1. Preparation of 2-fluoro-6-nitro-N-phenyl benzamide (Compound 2)

Compound 2-fluoro-6-nitro benzoic acid (5.0 g, 0.027 mol) and N, N-dimethyl formamide (0.5 mL) were added into a flask successively and dissolved with 20 mL dichloromethane. Then oxalyl chloride (5.1 g, 0.04 mol, 1.5 eq) was added slowly dropwise. The reaction solution was concentrated after stirring for 2 hours under room temperature. The slurry sample was dissolved in dioxane (10 mL) and cooled to 5° C. The solution was added dropwise to the hybrid system of dioxane and water (1:1, v:v, 30 mL) containing aniline (5 mL, 0.027 mol, 1 eq) and sodium bicarbonate (4.5 g, 0.054 mol, 2 eq). After addition, the reaction solution was warmed to room temperature and stirred for 60 min. Water was added and large amount of solid compounds were precipitated. The solid compounds were filtered and the filter cake was washed with water. After suction filtration, the filtrate was dried under fine vacuum at 50° C. for 24 hours, off-white solid target product (6.0 g, 85%) was obtained. $^1$H NMR (300 MHz, DMSO-d$_6$) δ 10.82 (s, 1H), 8.12 (d, J=7.7 Hz, 1H), 7.91-7.77 (m, 2H), 7.64 (d, J=7.7 Hz, 2H), 7.38 (t, J=7.9 Hz, 2H), 7.15 (t, J=7.4 Hz, 1H); ESI-MS m/z 261 (M+H)$^+$.

2. Preparation of (S)-[1-(2-fluoro-6-nitro-benzene formyl)-phenyl-ammonia formyl]-(1-d-propyl)-the amino acid tert-butyl ester (Compound 3)

2-fluoro-6-nitro-N-phenyl benzamide (7.8 g, 0.03 mol), N, N-dimethyl formamide (0.5 mL) and thionyl chloride (17.8 g, 0.15 mol, 5 eq) were sequentially added to a flask, warmed to 40° C., and then the reaction was stirred for 5 hours. The reaction liquid was concentrated to obtain brown sticky substance. The brown sticky substance was dissolved by 20 mL dichloromethane and was added dropwise to 50 mL dichloromethane solution containing (S)-2-t-Butyloxy carbonyl amide-2-d-butyrate (6.7 g, 0.033 mol, 1.1 eq) and triethylamine (3.4 g, 0.033 mol, 1.1 eq). The reaction mixture was stirred for 3 hours at room temperature and then filtered to remove the solids. The aqueous layer was washed with pure water, saturated sodium bicarbonate, pure water, 5% citric acid and saturated brine respectively. The organic layer was dried over anhydrous magnesium sulfate, and concentrated to obtain red sticky substance. The crude product was purified by silica gel column chromatography (10%-25% N-hexane/ethyl acetate) to get the desired white solid product compound 3 (8.0 g, 60%). ESI-MS m/z 447 (M+H)$^+$.

3. Preparation of (S)-[1-(5-fluoro-4-oxo-3-phenyl-3, 4-dihydroxy-quinazolin-2-yl)-(1-d-propyl)]-carbamic acid tert-butyl ester (Compound 4)

Compound (S)-[1-(2-fluoro-6-nitro-benzene formyl)-phenyl-ammonia formyl]-(1-d-propyl)-carbamic acid tert-butyl ester (4.5 g, 0.01 mol, 1 eq) and acetic acid (50 mL) were added into the flask successively. The temperature was kept under 20° C., and zinc powder (48.4 g, 740 mmol, 6 eq) was added in three portions. The reaction mixture was stirred for 2 hours at room temperature and then suction filtered. The filter cake was washed with acetic acid, and the filtrate was concentrated and dissolved in ethyl acetate, washed with pure water, saturated sodium bicarbonate and brine respectively, and was dried over anhydrous magnesium sulfate, concentrated to obtain residue. The residue was purified by silica gel column chromatography (10%-25% N-hexane/ ethyl acetate) to get the desired off-white bubbly solid product. $^1$H NMR (400 MHz, DMSO-d$_6$) δ 7.80 (s, 1H), 7.62-7.44 (m, 5H), 7.38 (d, J=7.6 Hz, 1H), 7.30 (m, 1H), 7.23 (d, J=7.6 Hz, 1H), 1.76-1.68 (m, 1H), 1.60-1.46 (m, 1H), 1.31 (s, 9H), 0.62 (t, J=7.2 Hz, 3H). ESI-MS m/z 399 (M+H)$^+$.

4. Preparation of (S)-2-(1-amino-1-d-propyl)-5-fluoro-3-phenyl quinazoline-4(3H)-ketone (Compound 5)

(S)-[1-(5-fluoro-4-oxo-3-phenyl-3,4-dihydroxy-quinazolin-2-yl)-(1-d-propyl)]-carbamic acid tert-butyl ester (1.99 g, 5 mmol) and dichloromethane (6 mL) were sequentially added to a flask. Trifluoroacetic acid was added (6 mL) under stirring. It was stirred at room temperature for 1 hour and then concentrated by high vacuum concentration. The residue was dissolved in methylene chloride and then 10% potassium carbonate solution was added until the pH reached 9 and layered. The aqueous layer was extracted with dichloromethane. The organic layers were combined, and washed with water and brine successively, and dried over anhydrous magnesium sulfate, concentrated to obtain off-white solid target product (1.4 g, 93%). $^1$H NMR (400 MHz, CDCl$_3$) δ 7.74-7.66 (m, 1H), 7.62-7.50 (m, 4H), 7.30-7.20 (m, 2H), 7.12-7.06 (m, 1H), 1.88-1.72 (m, 1H), 1.58-1.41 (m, 1H), 0.78 (t, J=7.2 Hz, 3H). ESI-MS m/z 299.1 (M+H)$^+$.

5. Preparation of (S)-2-(1-(9H-purin-6-yl-amino)-1-d-propyl)-5-fluoro-3-phenyl quinazoline-4(3H)-ketone (Compound 6)

(S)-2-(1-amino-1-d-propyl)-5-fluoro-3-phenyl quinazoline-4(3H)-ketone (1.2 g, 4 mmol, 1 eq), 6-bromine purine (0.88 g, 4.4 mmol, 1.1 eq), diisopropyl ethylamine (1.04 g, 8 mmol, 2 eq) and tertiary butyl alcohol was successively added to a flask. The reaction mixture was stirred for 30 hours at 80° C. The sample was concentrated to get solid crude product. The crude product was separated and purified by silica gel column chromatography (4% methanol/dichloromethane) to give the product as yellowish solid (1.0 g, 60%). $^1$H NMR (400 MHz, DMSO-d$_6$) δ 12.70 (s, 1H), 8.12 (s, 1H), 8.02 (s, 1H), 7.82-7.74 (m, 1H), 7.62-7.40 (m, 6H), 7.26-7.15 (m, 2H), 2.03-1.75 (m, 2H), 0.78 (t, J=7.2 Hz, 3H). ESI-MS m/z 417 (M+H)$^+$.

Example 2

Preparation of (S)-2-(1-(9H-purin-6-yl-amino)-1,2, 2-d$_3$-propyl)-5-fluoro-3-phenyl quinazoline-4(3H)-ketone (Compound 7)

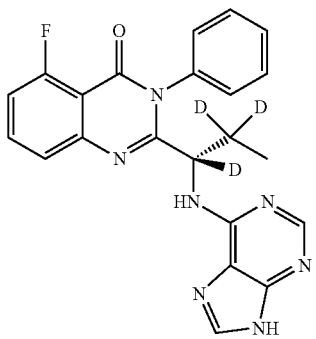 [SMILES: [2H]C([2H])(C)[C@]([2H])(Nc1ncnc2[nH]cnc12)c1nc2cccc(F)c2c(=O)n1-c1ccccc1]

The synthesis was conducted according to the method of example 1. The difference is: target product (compound 7) was obtained by replacing (S)-2-(t-Butyloxy carbonyl amide)-2-d-butyric acid with (S)-2-(t-Butyloxy carbonyl amide)-2,3,3-d3-butyric acid. ESI-MS m/z 419 (M+H)$^+$.

Example 3

Preparation of (S)-2-(1-(9H-purin-6-yl-amino)-1,2,2,3,3,3-d₆-propyl)-5-fluoro-3-phenyl quinazoline-4(3H)-ketone (Compound 8)

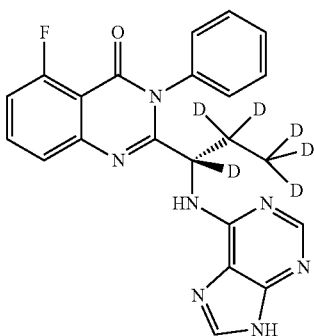 [SMILES: [2H]C([2H])([2H])C([2H])([2H])[C@]([2H])(Nc1ncnc2[nH]cnc12)c1nc2cccc(F)c2c(=O)n1-c1ccccc1]

The synthesis was conducted according to the method of example 1. The only difference is: target product (compound 8) was obtained by replacing (S)-2-(t-Butyloxy carbonyl amide)-2-d-butyric acid with (S)-2-(t-Butyloxy carbonyl amide)-2,3,3,4,4,4-d₆-butyric acid. ESI-MS m/z 422 (M+H)⁺.

Example 4

Preparation of (S)-2-(1-(9H-purin-6-yl-amino)-1,3,3,3-d₄-propyl)-5-fluoro-3-phenyl quinazoline-4(3H)-ketone (Compound 9)

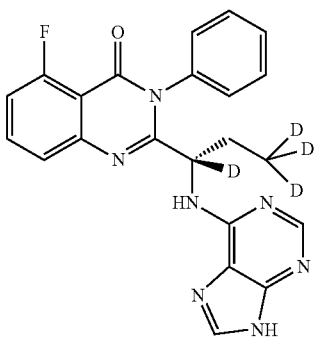 [SMILES: [2H]C([2H])([2H])C[C@]([2H])(Nc1ncnc2[nH]cnc12)c1nc2cccc(F)c2c(=O)n1-c1ccccc1]

The synthesis was conducted according to the method of example 1. The only difference is: target product (compound 9) was obtained by replacing (S)-2-(t-Butyloxy carbonyl amide)-2-d-butyric acid with (S)-2-(t-Butyloxy carbonyl amide)-2,4,4,4-d₄-butyric acid. ESI-MS m/z 422 (M+H)⁺.

Example 5

Preparation of (S)-2-(1-(9H-purin-6-yl-amino)-2,2,3,3,3-d₅-propyl)-5-fluoro-3-phenyl quinazoline-4(3H)-ketone (Compound 10)

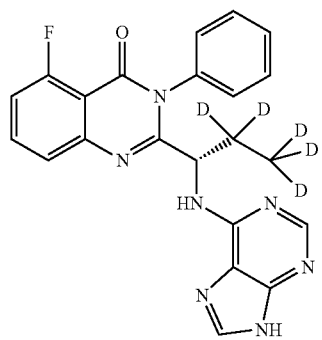 [SMILES: [2H]C([2H])([2H])C([2H])([2H])[C@H](Nc1ncnc2[nH]cnc12)c1nc2cccc(F)c2c(=O)n1-c1ccccc1]

The synthesis was conducted according to the method of example 1. The only difference is: target product (compound 10) was obtained by replacing (S)-2-(t-Butyloxy carbonyl amide)-2-d-butyric acid with (S)-2-(t-Butyloxy carbonyl amide)-3,3,4,4,4-d₅-butyric acid. ESI-MS m/z 421 (M+H)⁺.

Example 6

Preparation of (S)-2-(1-(9H-purin-6-yl-amino)-3,3,3-d₃-propyl)-5-fluoro-3-phenyl quinazoline-4(3H)-ketone (Compound 11)

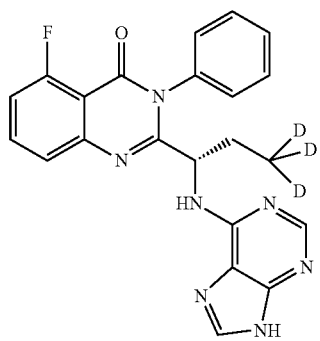

The synthesis was conducted according to the method of example 1. The only difference is: target product (compound 11) was obtained by replacing (S)-2-(t-Butyloxy carbonyl amide)-2-d-butyric acid with (S)-2-(t-Butyloxy carbonyl amide)-4,4,4-d₃-butyric acid. ESI-MS m/z 419 (M+H)⁺.

Example 7

Preparation of (S)-2-(1-(9H-purin-6-yl-amino)-2,2-d₂-propyl)-5-fluoro-3-phenyl quinazoline-4(3H)-ketone (Compound 12)

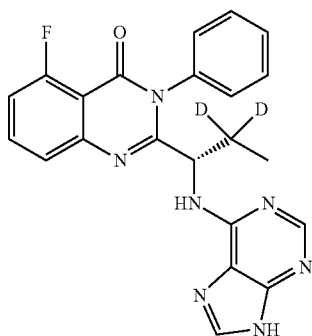 [SMILES: [2H]C([2H])(C)[C@H](Nc1ncnc2[nH]cnc12)c1nc2cccc(F)c2c(=O)n1-c1ccccc1]

The synthesis was conducted according to the method of example 1. The only difference is: target product (compound 12) was obtained by replacing (S)-2-(t-Butyloxy carbonyl amide)-2-d-butyric acid with (S)-2-(t-Butyloxy carbonyl amide)-3,3-d₂-butyric acid. ESI-MS m/z 418 (M+H)⁺.

Example 8

Preparation of (S)-2-(1-(9H-purin-6-yl-amino)-1-d-ethyl)-6-fluoro-3-phenyl quinazoline-4(3H)-ketone (Compound 13)

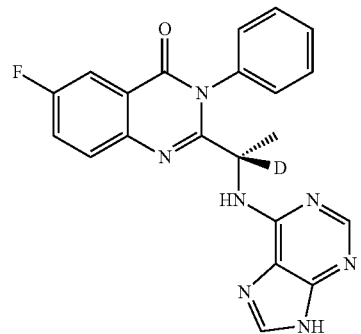 [SMILES: [2H][C@@](C)(Nc1ncnc2[nH]cnc12)c1nc2ccc(F)cc2c(=O)n1-c1ccccc1]

The synthesis was conducted according to the method of example 1. The only difference is: target product (compound 13) was obtained by replacing 2-fluoro-6-nitro benzoic acid with 3-fluoro-6-nitro benzoic acid, and replacing (S)-2-(t-Butyloxy carbonyl amide)-2-d-butyric acid with (S)-2-(t-Butyloxy carbonyl amide)-2-d-propionic acid. ESI-MS m/z 403 (M+H)⁺.

Example 9

Preparation of (S)-2-(1-(9H-purin-6-yl-amino)-1,2,2,2-d₄-ethyl)-6-fluoro-3-phenyl quinazoline-4(3H)-ketone (Compound 14)

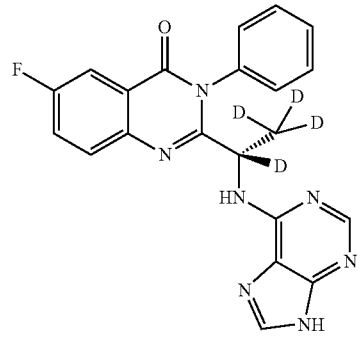 [SMILES: [2H]C([2H])([2H])[C@]([2H])(Nc1ncnc2[nH]cnc12)c1nc2ccc(F)cc2c(=O)n1-c1ccccc1]

The synthesis was conducted according to the method of example 1. The only difference is: target product (compound 14) was obtained by replacing 2-fluoro-6-nitro benzoic acid with 3-fluoro-6-nitro benzoic acid, and replacing (S)-2-(t-Butyloxy carbonyl amide)-2-d-butyric acid with (S)-2-(t-Butyloxy carbonyl amide)-2,3,3,3-d₄-propionic acid. ESI-MS m/z 406 (M+H)⁺.

Example 10

Preparation of (S)-2-(1-(9H-purin-6-yl-amino)-2,2,2-d₃-ethyl)-6-fluoro-3-phenyl quinazoline-4(3H)-ketone (Compound 15)

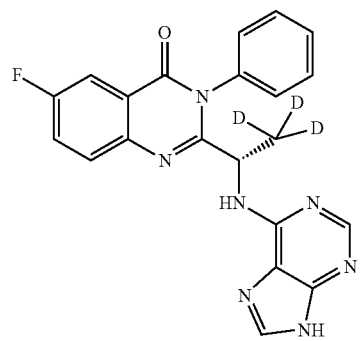 [SMILES: [2H]C([2H])([2H])[C@H](Nc1ncnc2[nH]cnc12)c1nc2ccc(F)cc2c(=O)n1-c1ccccc1]

The synthesis was conducted according to the method of example 1. The only difference is: target product (compound 15) was obtained by replacing 2-fluoro-6-nitro benzoic acid with 3-fluoro-6-nitro benzoic acid, and replacing (S)-2-(t-Butyloxy carbonyl amide)-2-d-butyric acid with (S)-2-(t-Butyloxy carbonyl amide)-3,3,3-d₃-propionic acid. ESI-MS m/z 405 (M+H)⁺.

Example 11

Preparation of (S)-2-(1-(9H-purin-8-d-6-yl-amino)-(1-d-propyl)-5-fluoro-3-phenyl quinazoline-4(3H)-ketone (Compound 16)

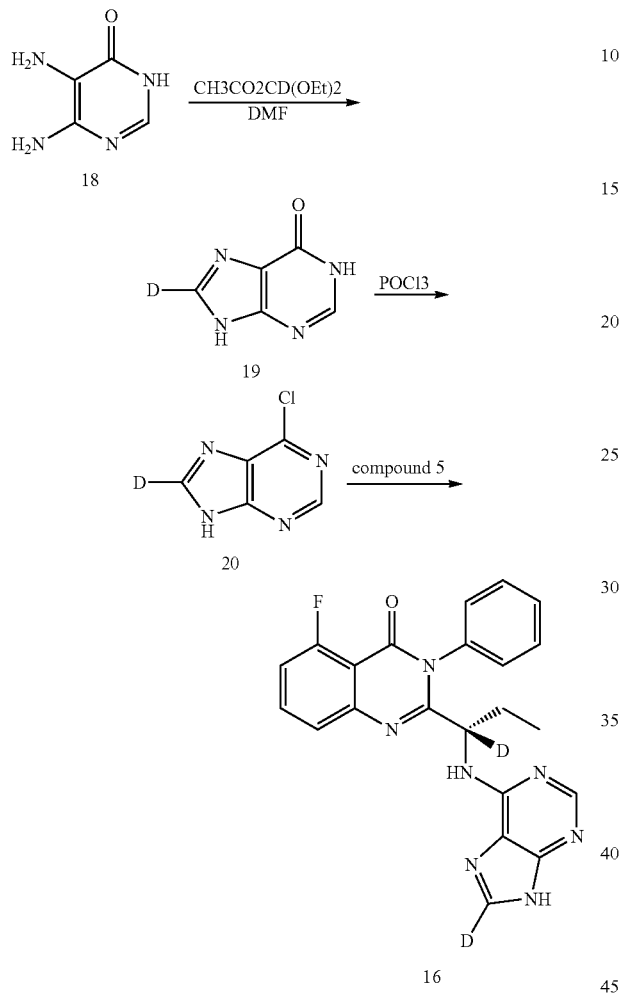

Preparation of 1,9-dihydro-6H-purine-6-ketone-8-d (Compound 19)

5,6-diaminopyrimidine-4(3H)-ketone (3.52 g, 0.028 mol) was suspended in formic acid (25 mL). The mixture was stirred while heating to reflux for 2 hours, and then concentrated to get yellow solid. Diethoxy acetate (methyl-d) ester (9.13 g, 0.056 mol), formic acid (2 mL) and N,N-dimethylformamide (50 mL) were added into the mixture. The reaction mixture was heated to reflux for 4 hours, and then concentrated. The concentrations were dissolved in acetonitrile and heated to reflux for 30 minutes, then cooled to 0° C., filtered and dried to obtain off-white solid product (35 g, yield: 78.3%). $^1$H NMR (D$_2$O/NaOD) 8.10 (s, 1H).

Preparation of 6-chloro-9H-purine-8-d (Compound 20)

Compound 1,9-dihydro-6H-purine-6-ketone-8-d (0.26 g, 1.9 mmol), phosphorus oxychloride (7 mL) and N, N-dimethyl aniline (0.7 mL) were added into flask successively. The mixture was heated to reflux for 25 minutes. Volatile organic compounds were removed by high vacuum concentration. The concentrations were cooled to −15° C. and dissolved in ammonia. After diatomite filtration, the obtained mixture was extracted with ethyl acetate and aether twice. The solution was cooled to 0° C. and diluted by pure water. Concentrated hydrochloric acid was used to adjust the pH to about 2. The solution was extracted by aether. The organic layer was neutralized by ammonia and then concentrated. The concentrations were prepared by preparative chromatography to give the desired product as off-white solid (0.22 g). $^1$H NMR (DMSO-d6) 8.75 (s, 1H).

Preparation of (S)-2-(1-(9H-purin-8-d-6-yl-amino)-(1-d-propyl))-5-fluoro-3-phenyl quinazoline-4(3H)-ketone (Compound 16)

Compound (S)-2-(1-amino-1-d-propyl)-5-fluoro-3-phenyl quinazoline-4(3H)-ketone (0.24 g, 0.8 mmol), 6-chloro-9H-purine-8-d (0.18 g, 0.88 mmol), diisopropyl ethylamine (0.21 g, 1.6 mmol) and tertiary butanol (2 mL) were added into a flask, warmed to 80° C. to stir for 30 hours. The reaction solution was concentrated to get the crude product. The concentrations were purified by silica gel column chromatography (4% methanol/dichloromethane) to obtain the desired yellowish solid product (0.25 g). ESI-MS m/z 418 (M+H)$^+$, 440 (M+Na)$^+$.

Example 12

Preparation of (S)-2-(1-(9H-purin-2,8-d$_2$-6-yl-amino)-(1-d-propyl))-5-fluoro-3-phenyl quinazoline-4(3H)-ketone (Compound 17)

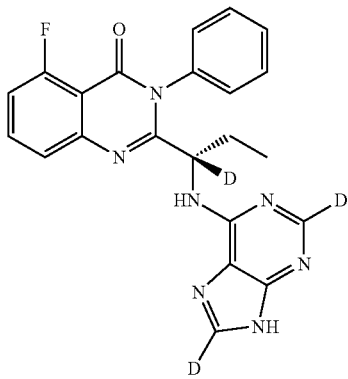 [SMILES: [2H]c1nc(N[C@@]([2H])(CC)c2nc3cccc(F)c3c(=O)n2-c2ccccc2)c2nc([2H])[nH]c2n1]

The synthesis was conducted according to the method of example 11. The only difference is: target product compound 17 was obtained by replacing 6-chloro-9H-purine-8-d with 6-chloro-2,8-d$_2$-purine. ESI-MS m/z 419 (M+H)$^+$.

Example 13

Preparation of (S)-2-(1-(9H-purin-2,8-d$_2$-6-yl-amino)-propyl)-5-fluoro-3-phenyl quinazoline-4(3H)-ketone (Compound 21)

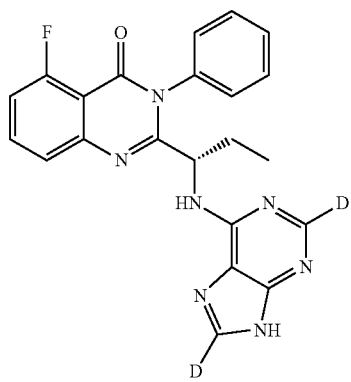 [SMILES: [2H]c1nc(N[C@@H](CC)c2nc3cccc(F)c3c(=O)n2-c2ccccc2)c2nc([2H])[nH]c2n1]

The synthesis was conducted according to the method of example 11. The only difference is: target product (compound 21) was obtained by replacing (S)-2-(1-amino-1-d-propyl)-5-fluoro-3-phenyl quinazoline-4(3H)-ketone with (S)-2-(1-amino propyl)-5-fluoro-3-phenyl quinazoline-4(3H)-ketone, and replacing 6-chloro-9H-purine-8-d with 6-chloro-2,8-d$_2$-purine. ESI-MS m/z 418 (M+H)$^+$.

Example 14

Preparation of (S)-2-(1-(9H-purin-8-d-6-yl-amino)-propyl)-5-fluoro-3-phenyl quinazoline-4(3H)-ketone (Compound 22)

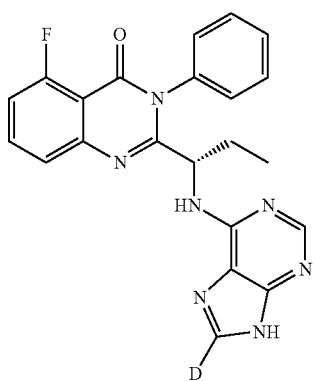 [SMILES: [2H]c1nc2c(N[C@@H](CC)c3nc4cccc(F)c4c(=O)n3-c3ccccc3)ncnc2[nH]1]

The synthesis was conducted according to the method of example 11. The only difference is: target product (compound 22) was obtained by replacing (S)-2-(1-amino-1-d-propyl)-5-fluoro-3-phenyl quinazoline-4(3H)-ketone with (S)-2-(1-aminopropyl)-5-fluoro-3-phenyl quinazoline-4(3H)-ketone, and replacing 6-bromine purine with 6-chloro-9H-purine-8-d. ESI-MS m/z 417 (M+H)$^+$.

Example 15

Pharmacokinetic Evaluation in Rats 4 male Sprague-Dawley rats (7-8 weeks old, approximately 210 g body weight), were divided into two groups with four in each group. A dose of 3 mg/kg of (a) the control compound (S)-2-(1-(9H-purin-6-yl-amino) propyl)-5-fluoro-3-phenyl quinazoline-4(3H)-ketone and (b) test compound: compounds prepared in example 1-14 was orally administrated for each time, and the difference in pharmacokinetics between the two groups was compared.

Rats were fed with standard feed, and given water ad libitum, and started to fast 16 hours before the test. The drug is dissolved with PEG400 and dimethylsulfoxide. Orbital blood collection was conducted at 0.25 hour, 0.5 hour, 1 hour, 2 hour, 4 hour, 6 hour, 8 hour, 12 hour, 24 hour and 36 hour after administration.

The rats are shortly anesthesiaed by inhalation of ether; 300 μL of orbital blood was collected into a test tube. There were 30 μL 1% heparin saline solutions in the test tube. Before use, test tubes were dried overnight at 60° C. After the blood sample was collected at the subsequent time point, rats were anesthetized with ether and euthanatized.

After the blood sample was collected, the tubes were gently inverted at least 5 times immediately to ensure adequate mixing, and placed on ice. At 4° C., blood samples were centrifuged at 5000 rpm for 5 minutes to separate plasma and red blood cells. 100 μL of plasma was pipetted into a clean plastic centrifuge tube, and the name of compounds and the time point was indicated. Plasma was stored at −80° C. before performing the analysis. The concentration of compound of the invention in plasma was determined with LC-MS/MS. The pharmacokinetic parameters were calculated based on the plasma concentration of compound in each animal at different time points.

It can be seen from the results that, compared with the control compound, compounds of the present invention are of longer half-life and higher exposure levels of plasma in animals, which has better pharmacodynamic and therapeutic effects.

Example 16

In Vitro Pharmacodynamics Evaluation to PI3K Kinases of the Compounds of the Invention The experiment of in vitro pharmacodynamics evaluation has been designed specifically according to the reference J. Med. Chem. 2013, 56, 1922-1939.

The results are shown in table 1. It can be seen that the compounds of the present invention have excellent inhibitory activity to PI3K kinase.

TABLE 1

| Compound | PI3Kδ kinase inhibitory activity (IC$_{50}$) |
|---|---|
| Example 1 | <20 nM |
| Example 2 | <20 nM |
| Example 3 | <20 nM |
| Example 4 | <20 nM |
| Example 5 | <20 nM |
| Example 6 | <20 nM |
| Example 7 | <20 nM |
| Example 8 | <20 nM |
| Example 9 | <20 nM |
| Example 10 | <20 nM |
| Example 11 | <20 nM |
| Example 12 | <20 nM |
| Example 13 | <20 nM |
| Example 14 | <20 nM |

Example 17

Pharmaceutical Composition

| | |
|---|---|
| Compound (Example 1-14) | 100 g |
| Starch | 130 g |
| Microcrystalline cellulose | 60 g |

The above substances were mixed by conventional methods, and then filled into general gelatin capsules to obtain 1000 capsules.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A deuterated quinazolinone compound of formula (I), or a pharmaceutically acceptable salt, hydrate or solvate thereof:

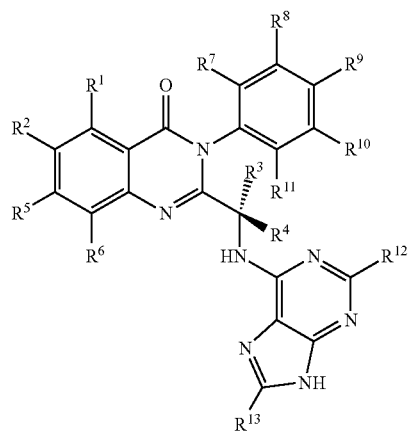

(I)

wherein $R^1$ is fluorine;

$R^3$ is selected from the group consisting of $CH_2CH_3$, $CD2CH_3$, $CH_2CD_3$ and $CD_2CD_3$;

each of $R^4$, $R^2$ and $R^{13}$ is independently hydrogen or deuterium; and each of $R^2$, $R^5$, $R^6$, $R^7$, $R^8$, $R^9$, $R^{10}$, and $R^{11}$ is hydrogen, with the proviso that at least one of $R^3$, $R^4$, $R^{12}$ and $R^{13}$ is deuterated or deuterium.

2. A deuterated quinazolinone compound of formula (I), or a pharmaceutically acceptable salt, hydrate or solvate thereof:

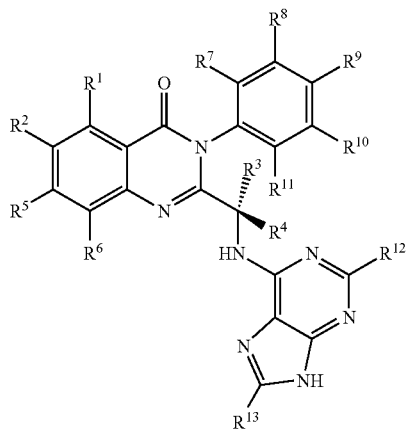

(I)

wherein $R^1$ is fluorine;

$R^3$ is selected from the group consisting of $CH_2CH_3$, $CD_2CH_3$, $CH_2CD_3$ and $CD_2CD_3$;

$R^4$ is deuterium;

each of $R^{12}$ and $R^{13}$ is independently hydrogen or deuterium; and each of $R^2$, $R^5$, $R^6$, $R^7$, $R^8$, $R^9$, $R^{10}$, and $R^{11}$ is hydrogen.

3. The compound of claim 1, wherein at least one of $R^{12}$ and $R^{13}$ is deuterium.

4. A compound selected from the group consisting of:

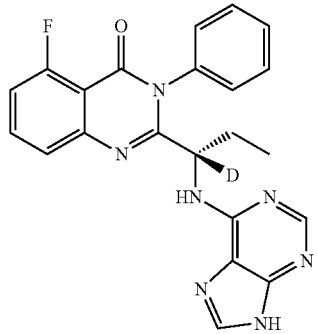

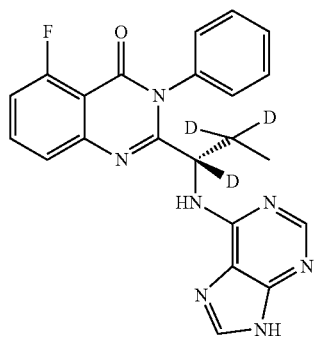

37
-continued
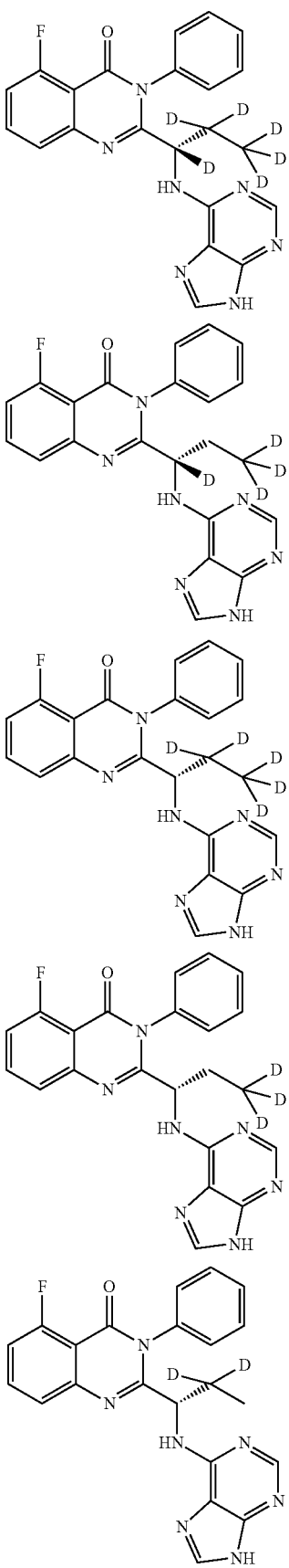
38
-continued
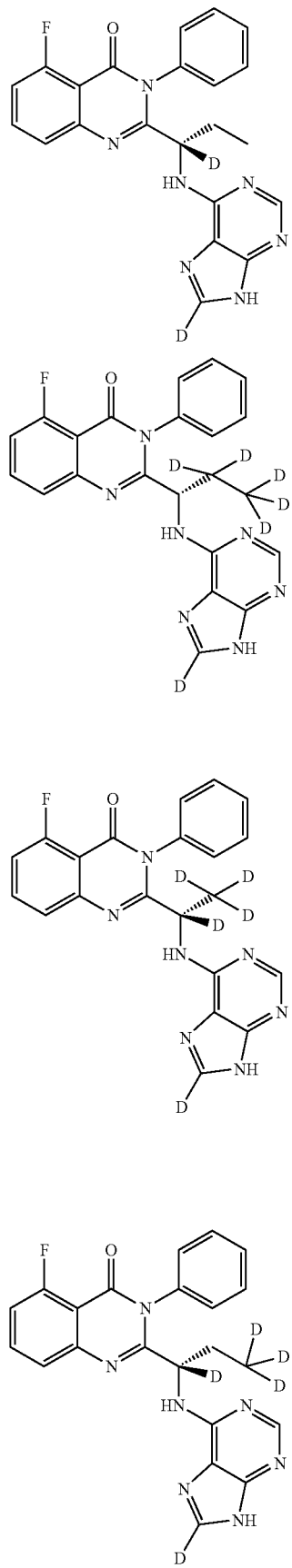

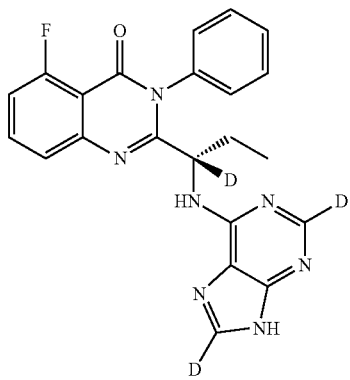

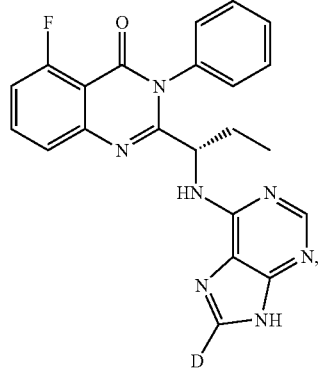

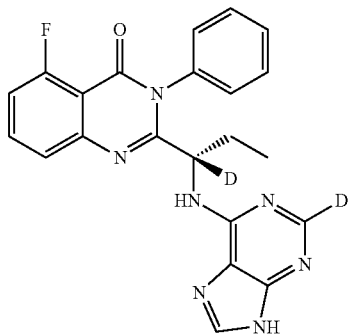

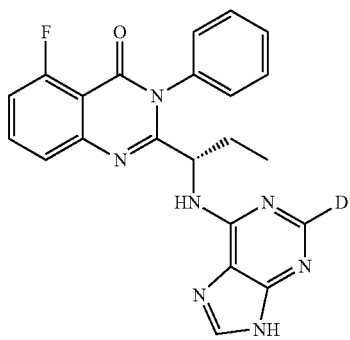

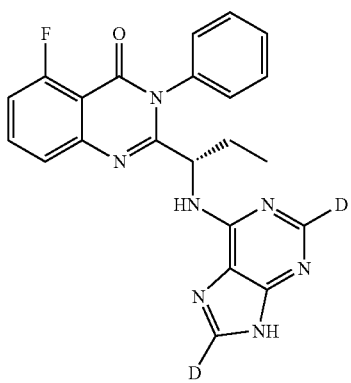

and or a pharmaceutically acceptable salt thereof.

5. A pharmaceutical composition, comprising a pharmaceutically acceptable carrier and the compound of claim 1, or a pharmaceutically acceptable salt, hydrate or solvate thereof.

6. The pharmaceutical composition of claim 5, wherein the pharmaceutical composition further comprises at least one additional therapeutic medicine, wherein the at least one additional therapeutic medicine is for treating leukemia or lymphoma.

7. A method of inhibiting PI3K protein kinases in a subject in need thereof, the method comprising administering the pharmaceutical composition of claim 5 to the subject.

8. The method of claim 7, wherein the method is for treating leukemia or lymphoma.

9. The pharmaceutical composition of claim 6, wherein the at least one additional therapeutic medicine is for treating a disease selected from the group consisting of chronic lymphocytic leukemia, acute lymphocytic leukemia, acute myeloid leukemia, multiple myeloma, chronic myeloid leukemia and non-Hodgkin's lymphoma.

10. The pharmaceutical composition of claim 9, wherein the disease is chronic lymphocytic leukemia or non-Hodgkin's lymphoma.

11. A pharmaceutical composition comprising a pharmaceutically acceptable carrier and the compound of claim 4, or pharmaceutically acceptable salt thereof.

12. A method of inhibiting PI3K kinases in a subject in need thereof, the method comprising administering the pharmaceutical composition of claim 11 to the subject.

13. The pharmaceutical composition of claim 11, wherein the pharmaceutical composition further comprises at least one additional therapeutic medicine, wherein the at least one additional therapeutic medicine is for treating leukemia or lymphoma.

14. The pharmaceutical composition of claim 11, wherein the pharmaceutical composition further comprises at least one additional therapeutic medicine, wherein the at least one additional therapeutic medicine is for treating a disease selected from the group consisting of chronic lymphocytic leukemia, acute lymphocytic leukemia, acute myeloid leukemia, multiple myeloma, chronic myeloid leukemia and non-Hodgkin's lymphoma.

15. A pharmaceutical composition comprising a pharmaceutically acceptable carrier and the compound of claim 2, or pharmaceutically acceptable salt, hydrate or solvate thereof.

16. The pharmaceutical composition of claim 15, wherein the pharmaceutical composition further comprises at least one additional therapeutic medicine, wherein the at least one additional therapeutic medicine is for treating leukemia or lymphoma.

17. The pharmaceutical composition of claim 15, wherein the pharmaceutical composition further comprises at least one additional therapeutic medicine, wherein the at least one additional therapeutic medicine is for treating a disease selected from the group consisting of chronic lymphocytic leukemia, acute lymphocytic leukemia, acute myeloid leukemia, multiple myeloma, chronic myeloid leukemia and non-Hodgkin's lymphoma.

18. The method of claim 12, wherein the method is for treating leukemia or lymphoma.

19. A method of inhibiting PI3K kinases in a subject in need thereof, the method comprising administering the pharmaceutical composition of claim 15 to the subject.

20. The method of claim 19, wherein the method is for treating leukemia or lymphoma.

* * * * *